United States Patent
Warner et al.

(10) Patent No.: US 11,352,554 B2
(45) Date of Patent: Jun. 7, 2022

(54) PHOTOCHROMIC WATER HARVESTING PLATFORM

(71) Applicant: WARNER BABCOCK INSTITUTE FOR GREEN CHEMISTRY, LLC, Wilmington, MA (US)

(72) Inventors: John C. Warner, Wilmington, MA (US); Srinivasa R. Cheruku, Lexington, MA (US); Sofia Trakhtenberg, Newton, MA (US)

(73) Assignee: Warner Babcock Institute for Green Chemistry, LLC, Mill Valley, CA (US)

( * ) Notice: Subject to any disclaimer, the term of this patent is extended or adjusted under 35 U.S.C. 154(b) by 95 days.

(21) Appl. No.: 16/313,299

(22) PCT Filed: Jun. 23, 2017

(86) PCT No.: PCT/US2017/038925
§ 371 (c)(1),
(2) Date: Dec. 26, 2018

(87) PCT Pub. No.: WO2017/223397
PCT Pub. Date: Dec. 28, 2017

(65) Prior Publication Data
US 2019/0153306 A1    May 23, 2019

Related U.S. Application Data

(60) Provisional application No. 62/353,925, filed on Jun. 23, 2016.

(51) Int. Cl.
| | | |
|---|---|---|
| *C09K 9/02* | (2006.01) | |
| *E03B 3/28* | (2006.01) | |
| *C07D 491/107* | (2006.01) | |

(52) U.S. Cl.
CPC ............ *C09K 9/02* (2013.01); *E03B 3/28* (2013.01); *C07D 491/107* (2013.01); *C09K 2211/1466* (2013.01); *Y02A 20/00* (2018.01)

(58) Field of Classification Search
CPC ..... C09K 9/02; C09K 2211/1466; E03B 3/28; Y02A 20/00; C07D 491/107

USPC .......................................................... 252/583
See application file for complete search history.

(56) References Cited

U.S. PATENT DOCUMENTS

| | | |
|---|---|---|
| 5,782,969 A | 7/1998 | Takagi |
| 2003/0099910 A1 | 5/2003 | Kim et al. |
| 2008/0261323 A1 | 10/2008 | Diamond et al. |
| 2010/0224867 A1 | 9/2010 | Heuft et al. |
| 2012/0082713 A1 | 4/2012 | Meyering et al. |

FOREIGN PATENT DOCUMENTS

| | | |
|---|---|---|
| CN | 1872533 A | 12/2006 |
| CN | 104495855 A | 4/2015 |
| WO | WO2009/121149 A1 | 10/2009 |

OTHER PUBLICATIONS

Zhou, Y-N., et al., "Light-Responsive Smart Surface with Controllable Wettability and Excellent Stability,"Langmuir 2014;30(41):12236-12242.*
International Preliminary Report on Patentability for PCT Patent App. No. PCT/US2017/038925 (dated Jan. 3, 2019).
Supplementary European Search Report for European Patent App. No. 17816260.8 (dated Dec. 10, 2019).
Chen, L., et al., "A Light-Responsive Release Platform by Controlling the Wetting Behavior of Hydrophobic Surface," ACS Nano 2014;8(1):744-751.
Pala, R., et al., "A Nonvolatile Plasmonic Switch Employing Photochromic Molecules," Nano Letters 2008;8(5):1506-1510.
International Search Report and Written Opinion for PCT Patent App. No. PCT/US2017/038925 (dated Sep. 21, 2017).
James, M., et al., "Nanoscale Water Condensation on Click-Functionalized Self-Assembled Monolayers," Langmuir 2011;27(17):10753-10762.
First Office Action from Chinese Patent App. No. 201780051611.0 (dated Jun. 13, 2021) with English translation thereof.

* cited by examiner

*Primary Examiner* — Ling Siu Choi
*Assistant Examiner* — Ronald Grinsted
(74) *Attorney, Agent, or Firm* — Cermak Nakajima & McGowan LLP; Malcolm K. McGowan

(57) ABSTRACT

The application discloses compounds, compositions, films and devices comprising the compounds and compositions, and their methods of use for harvesting water.

5 Claims, 2 Drawing Sheets

A

B

PHOTOCHROMIC WATER HARVESTING PLATFORM

CROSS-REFERENCE TO RELATED APPLICATIONS

This application is a National Stage Entry of PCT/US2017/038925, filed Jun. 23, 2017, which claims priority from U.S. Provisional patent application 62/353,925, filed Jun. 23, 2016. The contents of these priority applications are incorporated herein by reference in their entirety.

BACKGROUND

Plants and animals survive in desert climates by utilizing a variety of water-harvesting mechanisms. Self-irrigating plants, such as desert rhubarb (*Rheum palaestinum*, native to the Negev desert), use their leaves to collect rainwater over a large area, and grooves in the leaves to direct the collected water towards the roots of the plant. The fog-harvesting grass (*Stipagrostis sabulicola*) and the Namib desert beetle (*Stenocara gracilipes*) both make their home in the Namib desert. In both *S. sabulicola* and *S. gracilipes*, the unique combinations of surface wettability properties and grooved morphology on the collection surfaces (leaf or wing cover) allow for efficient water collection from fog droplets and transport of the water to roots or mouth.

Utilizing the principles of surface wettability and morphology in an artificial system would avoid the need for transporting water to arid regions, decrease the costs for managing droughts, and generally improve quality of life. The systems utilized by *S. sabulicola* and *S. gracilipes* are inherently inefficient, since the hydrophilic areas are used for water capture, while the hydrophobic areas are used for water transport. To address this inefficiency, a new approach utilizing light-switchable photochromic surfaces for water collection and delivery is disclosed herein.

SUMMARY

There is a need for systems and compositions that address these technological challenges.

In one embodiment, there is provided a photoactive film, thermally active film or electrically-active film, or a combination thereof, wherein the film is deposited on a surface, wherein the film or films comprise a compound having a ground state that reversibly converts to its activated or zwitterionic form upon exposure to light or heat or an electric field, or a combination of light, heat and/or electric field, wherein the zwitterionic form or activated state of the compound is more polar than the ground state of the compound.

In one embodiment, there is provided a photoactive, thermally active or electrically-active film, wherein the compound is of the formula I:

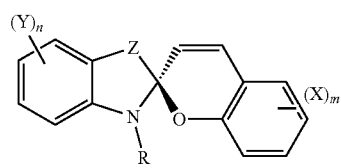

I wherein:

m is 0, 1, 2, 3 or 4;

n is 0, 1, 2, 3 or 4;

R is H or is selected from the group consisting of substituted or unsubstituted $C_{1-22}$ alkyl, substituted or unsubstituted $C_{6-10}$ aryl, substituted or unsubstituted —$C_{1-6}$ alkyl-$C_{6-10}$ aryl, substituted or unsubstituted $C_{1-22}$ alkylC(O)—, substituted or unsubstituted $C_{1-22}$ alkylS(O)$_{1-2}$—, substituted or unsubstituted $C_{1-22}$ alkylNR'C(O)— and substituted or unsubstituted $C_{1-22}$ alkoxyC(NR")—, or a polymer;

each X is independently H or is selected from the group consisting of halo, —CN, —NO$_2$, —COOH, —SH, —OH, substituted or unsubstituted $C_{1-6}$ alkyl, substituted or unsubstituted $C_{6-10}$ aryl, substituted or unsubstituted —$C_{1-6}$ alkyl-$C_{6-10}$ aryl, substituted or unsubstituted —$C_{1-6}$ alkylC(O)—, substituted or unsubstituted —$C_{1-6}$ alkylS(O)$_{1-2}$—, substituted or unsubstituted —$C_{1-6}$ alkylNR'C(O)— and substituted or unsubstituted $C_{1-6}$ alkoxyC(NR")—;

each Y is independently H or is selected from the group consisting of halo, —CN, —NO$_2$, —COOH, —SH, —OH, substituted or unsubstituted $C_{1-6}$ alkyl, substituted or unsubstituted $C_{5-10}$ aryl, substituted or unsubstituted —$C_{1-6}$ alkyl-$C_{6-10}$ aryl, substituted or unsubstituted $C_{1-6}$ alkylC(O)—, substituted or unsubstituted $C_{1-6}$ alkylS(O)$_{1-2}$—, substituted or unsubstituted $C_{1-6}$ alkylNR'C(O)— and substituted or unsubstituted $C_{1-6}$ alkoxyC(NR")—;

Z is —O—, —S—, —C(O)—, —C(S)—, C(NR')—, S(O)$_{1-2}$—, —NR'— and —CR'R"—; and

R' and R" are each independently selected from the group consisting of H, substituted or unsubstituted $C_{1-2}$ alkyl and substituted and unsubstituted —$C_{1-6}$ alkyl-$C_{6-10}$ aryl.

In one variation of the compound of the formula I, R is n-$C_{18}H_{37}$ or n-$C_{22}H_{45}$. In one aspect, the film may comprise of the compound of the formula I mixed in various ratios with one or more compounds or material. The mixed compound, compounds or material may be selected so as to impart other functional properties, such as film-forming ability, adhesion or water resiliency, to the film and or to a device. In one aspect, the material may include one or more polymers or polymeric materials. In one aspect, the compound of the formula I may be dissolved or mixed with or mixed in the material.

In one embodiment of the above, R comprises of a linking group that covalently attaches the compound to a polymer or polymer backbone, resulting in the compound being a part of a photoactive polymer, a thermally active or electrically active polymer, such as the polymer compound of the formula II:

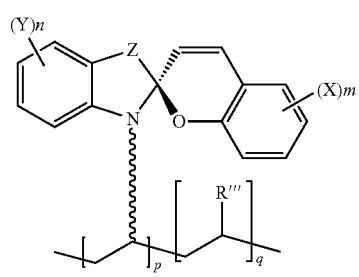

II wherein:

∿∿ comprises a linking group, m is 0, 1, 2, 3 or 4;

n is 0, 1, 2, 3 or 4;

each X is independently H or is selected from the group consisting of halo, —CN, —NO$_2$, —COOH, —SH, —OH, substituted or unsubstituted C$_{1-6}$ alkyl, substituted or unsubstituted C$_{6-10}$ aryl, substituted or unsubstituted —C$_{1-6}$ alkyl-C$_{6-10}$ aryl, substituted or unsubstituted —C$_{1-6}$ alkylC(O)—, substituted or unsubstituted —C$_{1-6}$ alkylS(O)$_{1-2}$—, substituted or unsubstituted —C$_{1-6}$ alkylNR'C(O)— and substituted or unsubstituted C$_{1-6}$ alkoxyC(NR")—;

each Y is independently H or is selected from the group consisting of halo, —CN, —NO$_2$, —COOH, —SH, —OH, substituted or unsubstituted C$_{1-6}$ alkyl, substituted or unsubstituted C$_{5-10}$ aryl, substituted or unsubstituted —C$_{1-6}$ alkyl-C$_{6-10}$ aryl, substituted or unsubstituted C$_{1-6}$ alkylC(O)—, substituted or unsubstituted C$_{1-6}$ alkylS(O)$_{1-2}$—, substituted or unsubstituted C$_{1-6}$ alkylNR'C(O)— and substituted or unsubstituted C$_{1-6}$ alkoxyC(NR")—;

Z is —O—, —S—, —C(O)—, —C(S)—, C(NR')—, S(O)$_{1-2}$—, —NR'— and —CR'R"—;

R' and R" are each independently selected from the group consisting of H, substituted or unsubstituted C$_{1-6}$ alkyl and substituted and unsubstituted —C$_{1-6}$ alkyl-C$_{6-10}$ aryl;

R'" is a substituent on the polymer, p is 0 or 1,000 to 100,000; and q is 0 or 1,000 to 100,000.

In one aspect of the above polymer compound, p is 1,000 to 50,000, 1,000 to 25,000, 1,000 to 20,000 or 1,000 to 10,000. In another aspect, p is 25,000 to 100,000, 25,000 to 75,000, or about 50,000.

In another aspect, q is 1,000 to 50,000, 1,000 to 25,000, 1,000 to 20,000 or 1,000 to 10,000. In another aspect, q is 25,000 to 100,000, 25,000 to 75,000, or about 50,000. In another aspect, the molecular weight of the polymer is 1,000 to 700,000 daltons, 1,000 to 500,000 daltons, 10,000 to 300,000 daltons, 20,000 to 100,000 daltons, 30,000 to 75,000 daltons or about 50,000 daltons. In one aspect, R'" is selected from the group consisting of —OC(O)CH$_3$, —OH, —OMe, —C$_{1-6}$ alkyl, —C$_6$H$_5$, —CF$_3$, —OCF$_3$ and —C(O)CH$_3$, or a mixture thereof. In another aspect, the polymer is attached to the nitrogen atom (N) of the compound by a group selected from —C$_{1-22}$ alkyl-, —C$_{6-10}$ aryl-, —C$_{1-6}$ alkyl-C$_{6-10}$ aryl-, —C$_{1-22}$ alkylC(O)—, —C(O)—, —C$_{1-22}$ alkylS(O)$_{1-2}$—, —C$_{1-22}$ alkylNR'C(O)—, —C$_{1-22}$ alkoxyC(NR")—, —S(O)$_{1-2}$—, —NR'C(O)— and —C(NR")—, or a combination thereof.

In one embodiment, the polymer is selected from the group consisting of polyethylene (LDPE or HDPE), polypropylene, poly(vinyl chloride), poly(vinylidene chloride), polystyrene, polyacrylonitrile, polytetrafluoroethylene (PTFE, Teflon), poly(methyl methacrylate) (PMMA), poly(vinyl acetate) (PVAc), polyisoprene, polychloroprene, poly(oxyethylene) (POE), poly(oxy-1,2-ethanediyloxycarbonyl-1,4-phenylenecarbony (PET), poly[amino(1-oxo-1,6-hexanediyl)], polystyrene, ethyl-vinyl-acetate (EVA), polylactide (PLA), polyhydroxyalkanoates (PHA), polyhydroxybutyrate (PHB), poly-L-lactide (PLLA), PDLA (poly-D-lactide) or mixtures thereof.

In another aspect of the above, the polymer or polymer film or films may be deposited on a surface of a base material such as ceramic, a metal such as copper, steel, stainless steel, iron or a plastic. In one variation of the above, the base material is part of a device. In one aspect, the device is a water-collecting device, and may comprise one or more panels.

In one embodiment, the base material may comprise a panel or series of panels configured to collect water. In one aspect, the panel or series of panels may comprise tiles such as roofing tiles. In another embodiment, the base material may be configured with an electric connection such as wires to an energy source, such as a battery or electricity source, for activating the compound or the film comprising the compound. In another embodiment, the panels may be configured to be connected to a water storage container, such as a storage tank for collecting and storing water.

In one aspect, the properties of the polymer II can be altered by the variation of the p:q ratio of the units that comprise the polymer. The properties of the polymer II can also be altered by variation of the molecular weight (chain length, or total number of p and q units in the polymer) of the polymer. The polymer may be a copolymer, such as a block polymer, such as a diblock or triblock copolymer, a graph polymer, an alternating polymer or mixtures thereof.

The properties of the polymer II can also be altered by variation of the linking group attaching the compound to the polymer backbone. In one aspect, the properties of the polymer II can also be altered by variation of the R'" substituent selected from acetate (—CO$_2$CH$_3$) or phenyl (—C$_6$H$_5$).

In another embodiment, there is provided a device comprising a photoactive film, a thermally active or an electrically-active film, or a combination thereof, wherein the film or films may be deposited on a surface of the device, wherein the film or films comprise a compound having a ground state that reversibly converts to its activated or zwitterionic form upon exposure to light or heat or an electric field or a combination of light, heat and an electric field, wherein the zwitterionic form or activated state of the compound is more polar than the ground state form of the compound.

As used herein, the term "activated state" of the compound is used interchangeably with the "zwitterionic form" of the compound. In the more polar form, the compound or the film comprising the compound, is more hydrophilic and collects water or moisture from the environment, the atmosphere or the humidity in the air.

In one aspect of the device, the above photoactive film, thermally active film and/or electrically-active active film or films, wherein the compound is of the formula I:

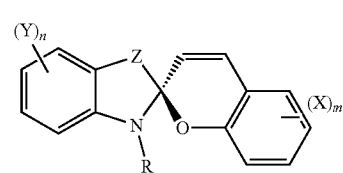

m is 0, 1, 2, 3 or 4;

n is 0, 1, 2, 3 or 4;

R is H or is selected from the group consisting of substituted or unsubstituted C$_{1-22}$ alkyl, substituted or unsubstituted C$_{6-10}$ aryl, substituted or unsubstituted —C$_{1-6}$ alkyl-C$_{6-10}$ aryl, substituted or unsubstituted C$_{1-22}$ alkylC(O)—, substituted or unsubstituted C$_{1-22}$ alkylS(O)$_{1-2}$—, substituted or unsubstituted C$_{1-22}$ alkylNR'C(O)— and substituted or unsubstituted C$_{1-22}$ alkoxyC(NR")—, or a polymer;

each X is independently H or is selected from the group consisting of halo, —CN, —NO$_2$, —COOH, —SH, —OH, substituted or unsubstituted C$_{1-6}$ alkyl, substituted or unsubstituted C$_{6-10}$ aryl, substituted or unsubstituted —C$_{1-6}$ alkyl- $C_{6-10}$ aryl, substituted or unsubstituted —$C_{1-6}$ alkylC(O)—, substituted or unsubstituted —$C_{1-6}$ alkylS(O)$_{1-2}$—, substituted or unsubstituted —$C_{1-6}$ alkylNR'C(O)— and substituted or unsubstituted $C_{1-6}$ alkoxyC(NR")—;

each Y is independently H or is selected from the group consisting of halo, —CN, —NO$_2$, —COOH, —SH, —OH, substituted or unsubstituted $C_{1-6}$ alkyl, substituted or unsubstituted $C_{5-10}$ aryl, substituted or unsubstituted —$C_{1-6}$ alkyl-$C_{6-10}$ aryl, substituted or unsubstituted $C_{1-6}$ alkylC(O)—, substituted or unsubstituted $C_{1-6}$ alkylS(O)$_{1-2}$—, substituted or unsubstituted $C_{1-6}$ alkylNR'C(O)— and substituted or unsubstituted $C_{1-6}$ alkoxyC(NR")—;

Z is —O—, —S—, —C(O)—, —C(S)—, C(NR')—, S(O)$_{1-2}$—, —NR'— and —CR'R"—; and

R' and R" are each independently selected from the group consisting of H, substituted or unsubstituted $C_{1-6}$ alkyl and substituted and unsubstituted —$C_{1-6}$ alkyl-$C_{6-10}$ aryl.

In one aspect of the compound, m is 0, 1 or 2 and n is 0, 1 or 2.

In another aspect, the device is configured for harvesting water from humid air and/or fog. In another aspect of the above, the device comprises a surface where wettability of the surface of the device can be altered by exposure of the device to light. In one aspect, the light is selected from the group consisting of ultraviolet, visible and infrared. In another aspect, the conversion of the compound from the ground state to the activated or zwitterionic state is reversible, and may be performed by exposure of the device to heat, and/or to light, and/or by electrical means such as a charge or current, and/or in combination with other methods for conversion of the ground state to the activated or zwitterionic state.

In another aspect of the device, the wettability of the film is reversibly altered or activated by light, such as sunlight, and deactivated in the absence of light, such as at dust or in the absence of sunlight. In one aspect of the above, the wettability of the film or film surface may be reversible by the application or removal of the light source, the heat source and/or the electrical source.

In another embodiment of the above, the device is rotated by wind or tide or river flow or wave action or any combination of the above, while the film is repeatedly activated/de-activated by intermittent exposure to sunlight.

In another embodiment, there is provided a method for capturing and/or adhesion or collecting of water droplets and/or condensation of water vapor onto a surface of a film, comprising: exposing a device comprising photoactive, thermally active and/or electrically-active or a combination of photoactive, thermally active and/or electrically active film deposited on a surface of the device, wherein the film comprises a compound having a ground state that reversibly converts to its activated or zwitterionic form upon exposure to light, heat, an electric field or a combination of light, heat and/or electric field, wherein the zwitterionic form or activated state or activated form of the compound is more polar than the ground state of the compound, to heat, light, or electric field, or a combination of heat, light and/or electric field, to the activated or zwitterionic form for a sufficient period of time to condense moisture or water on the surface of the film; and continuously collecting the water formed on the surface of the device.

In one aspect of the above method, the compound is of the formula I:

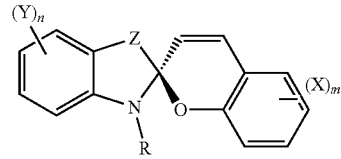

wherein:
m is 0, 1, 2, 3 or 4;
n is 0, 1, 2, 3 or 4;
R is H or is selected from the group consisting of substituted or unsubstituted $C_{1-22}$ alkyl, substituted or unsubstituted $C_{6-10}$ aryl, substituted or unsubstituted —$C_{1-6}$ alkyl-$C_{6-10}$ aryl, substituted or unsubstituted $C_{1-22}$ alkylC(O)—, substituted or unsubstituted $C_{1-22}$ alkylS(O)$_{1-2}$—, substituted or unsubstituted $C_{1-22}$ alkylNR'C(O)— and substituted or unsubstituted $C_{1-22}$ alkoxyC(NR")—, or a polymer;

each X is independently H or is selected from the group consisting of halo, —CN, —NO$_2$, —COOH, —SH, —OH, substituted or unsubstituted $C_{1-6}$ alkyl, substituted or unsubstituted $C_{6-10}$ aryl, substituted or unsubstituted —$C_{1-6}$ alkyl-$C_{6-10}$ aryl, substituted or unsubstituted —$C_{1-6}$ alkylC(O)—, substituted or unsubstituted —$C_{1-6}$ alkylS(O)$_{1-2}$—, substituted or unsubstituted —$C_{1-6}$ alkylNR'C(O)— and substituted or unsubstituted $C_{1-6}$ alkoxyC(NR")—;

each Y is independently H or is selected from the group consisting of halo, —CN, —NO$_2$, —COOH, —SH, —OH, substituted or unsubstituted $C_{1-6}$ alkyl, substituted or unsubstituted $C_{5-10}$ aryl, substituted or unsubstituted —$C_{1-6}$ alkyl-$C_{6-10}$ aryl, substituted or unsubstituted $C_{1-6}$ alkylC(O)—, substituted or unsubstituted $C_{1-6}$ alkylS(O)$_{1-2}$—, substituted or unsubstituted $C_{1-6}$ alkylNR'C(O)— and substituted or unsubstituted $C_{1-6}$ alkoxyC(NR")—;

Z is —O—, —S—, —C(O)—, —C(S)—, —C(NR')—, —S(O)$_{1-2}$—, —NR'— and —CR'R"—; and

R and R" are each independently selected from the group consisting of H, substituted or unsubstituted $C_{1-6}$ alkyl and substituted and unsubstituted —$C_{1-6}$ alkyl-$C_{6-10}$ aryl.

In one aspect, the spiropyrans disclosed in the present application are photochromic molecules. In their ground state, the molecules are charge neutral, but when irradiated with the appropriate wavelength of light (with energy hv, where h is Planck's constant and v is the frequency of the light corresponding to the appropriate wavelength) for example, they undergo a ring opening process (a photoreaction) to form a charged zwitterionic "activated form". For example, the activation of the spiropyran to the merocyanine form may also be effected by application of heat (thermochromism) and/or by an electric field (electrochromism) and/or by other processes.

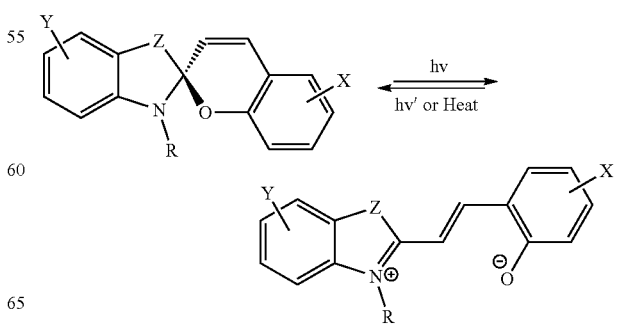

These reactions are reversible, and may occur either spontaneously under ambient thermal conditions, and/or with applied heat, and/or when irradiated by a different wavelength of light (with energy hv'), and/or by removal of the electric field, the molecules revert to their original form. The physical properties of the two forms of the compound are very different. The ground state of the compound is typically neutral, nonpolar and colorless (hv is typically ultraviolet light). On the other hand, the activated state or activated form is zwitterionic, polar and often highly colored (hv' is typically visible light).

The various properties of these compounds can be tailored by synthetically altering the X- and Y-substituents and the substitution pattern around the molecule. One such property is the compound's relative affinity for water. The ground state of the compound is hydrophobic and repels water, while the activated state or the activated form of the compound is hydrophilic and attracts water.

Accordingly, the ground state of a film or surface containing the compound is hydrophobic and repels water, while the film or surface containing the compound in the activated form of the compound is hydrophilic and attracts water.

Airborne water droplets and/or water vapor molecules contacting a hydrophobic surface are unlikely or less likely to adhere to the compound or the film containing the compound, and thus, remain on the surface. However, water that is present on a hydrophobic surface will "bead up," resulting in contact angles between the resulting beads of water and the hydrophobic surface that are large, typically greater than 90°. Airborne water droplets and/or water vapor molecules contacting a hydrophilic surface are likely to adhere and remain on the surface. In addition, water droplets that are present on a hydrophilic surface will "spread out," resulting in contact angles between the surface of the water droplet and the hydrophilic surface that are small, typically less than 90°.

As provided herein, there is provided a novel design of a film, such as a thin film, that oscillates between the ground state and the activated state or the activated form in such a way that in the active form, the film "captures" water and in the ground state it "releases" water. Such process is illustrated in one aspect of the application in Figure 2, using light as an activator.

While the fundamental principles of this process are clear, there are various permutations and variations of the present process that fall within the scope of the present disclosure. Through a set of designed iterations by variation in the nature of the compounds, the nature and type of substituents –X and –Y, and the nature and methods of attaching or applying the film to a particular surface, we establish the optimum water capacity and cycle time. Such non-exclusive systems or products that are embodied in the present application include, for example, municipal water collection devices that function in response to daylight/night time cycling or that function in response to wind- or tide-controlled mechanical shading that can cycle sun/shade at a faster rate.

As described herein, mechanistic interpretation is useful in order to illustrate the concepts and provide information on the various embodiments and aspects of the present application. However it is understood that the invention may also operate by a different mechanism or by a combination of various mechanisms not necessarily including the one described herein. Also under most circumstances it may not be possible to conclusively prove which mechanism is responsible for the observed effects. Therefore the provided above mechanistic interpretation is not to be interpreted as being either exclusive or limiting.

The following embodiments, aspects and variations thereof are exemplary and illustrative are not intended to be limiting in scope.

In one embodiment the device described herein is a device that is constructed for harvesting water from humid air and/or fog.

In another embodiment, there is provided a device comprising a surface which wettability (water contact angle either advancing or receding or both) can be altered by exposure to light (ultraviolet, visible or infrared).

In another embodiment, there is provided a method wherein the alteration or the conversion of one state from the other state, can be reversed either by exposure to heat and/or to light of a different wavelength or used in combination with other methods.

In another embodiment, there is provided a device comprising a surface or a film, such as a photoactive surface, for which wettability (water-surface contact angle either advancing or receding or both) can be reversibly altered by naturally occurring events, for example, wherein the surface is activated by sunlight (i.e., during day time) and deactivated during the night or in the absence of sunlight; or alternatively, where the components comprising the system or device are rotated by wind or tide or river flow or wave action or any combination of the above, while the surface, such as the photoactive surface is repeatedly activated/deactivated by intermittent exposure to sunlight.

In another embodiment, there is provided a coating composition comprising of a molecule or compound that becomes zwitterionic upon exposure to light, heat or a charge.

In another embodiment, there is provided a coating composition comprising of a molecule which becomes zwitterionic upon exposure to light and is presented in the scheme above.

As provided herein, the various embodiments and aspect of the present application using photochromic materials and polymer coatings, a system is structured to provide a cost effective technology to purify water. The technologies disclosed in the present documents are incorporated herein by reference in their entirety. Dynamic control of noncovalent interactions in mesoscale assembly: Green chemistry in action; Arundhati Undurti; John C. Warner; Abstracts of Papers, 225th ACS National Meeting, New Orleans, La., United States, Mar. 23-27, 2003 (2003), IEC-147; Reaction design and environmentally benign synthesis; John IV Pyers; John C. Warner; Amy S. Cannon; Abstracts of Papers, 225th ACS National Meeting, New Orleans, La., United States, Mar. 23-27, 2003 (2003), IEC-151.

The foregoing examples of the related art and limitations are intended to be illustrative and not exclusive. Other limitations of the related art will become apparent to those of skill in the art upon a reading of the specification and a study of the drawings or figures as provided herein.

In addition to the exemplary embodiments, aspects and variations described above, further embodiments, aspects and variations will become apparent by reference to the drawings and figures and by examination of the following descriptions.

BRIEF DESCRIPTION OF THE DRAWINGS

FIG. 1A is a schematic illustration of water droplets beading up on a hydrophilic film in the ground state and spreading out on an activated hydrophilic film; FIG. 1B shows that, in a bead of water on a hydrophilic film in the ground state, the contact angle is greater than 90°, while on an activated hydrophilic film, the contact angle is less than 90°.

FIG. 2 is a schematic illustration showing a thin film as described herein, which oscillates between the ground(hydrophobic) state and the activated (hydrophilic) state depending on the light contacting the surface.

DETAILED DESCRIPTION

Definitions

Figure 1:
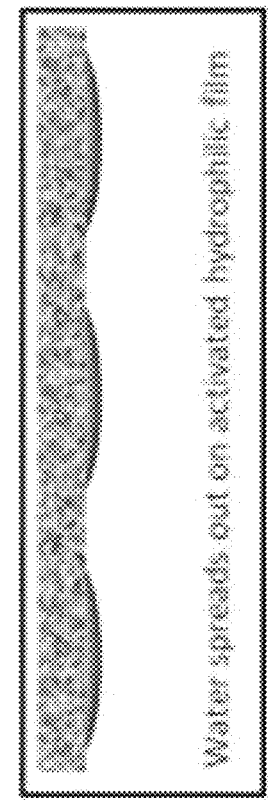
FIG. 1.
Figure 1:
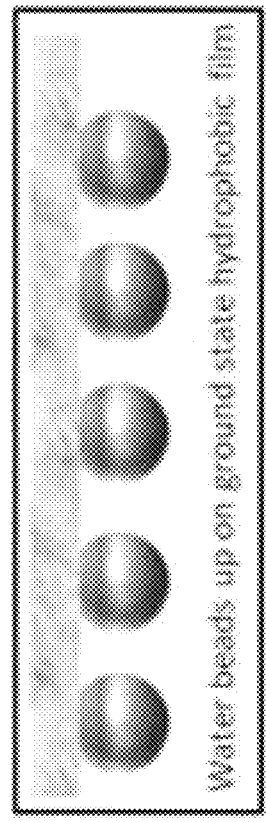
Figure 1:
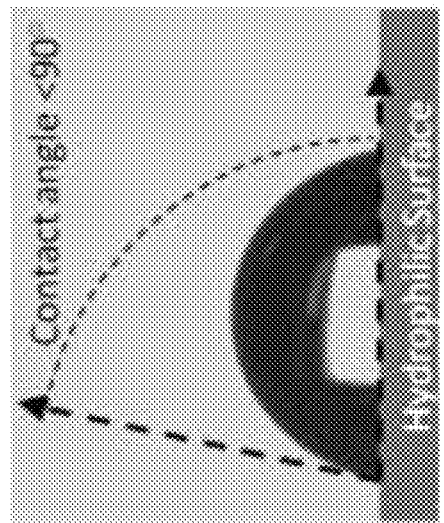
Figure 1:
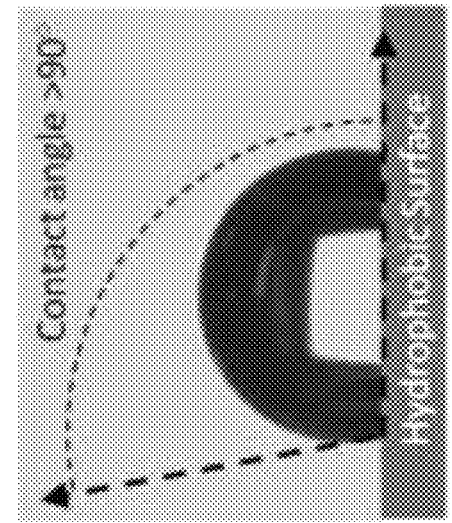
Figure 2:
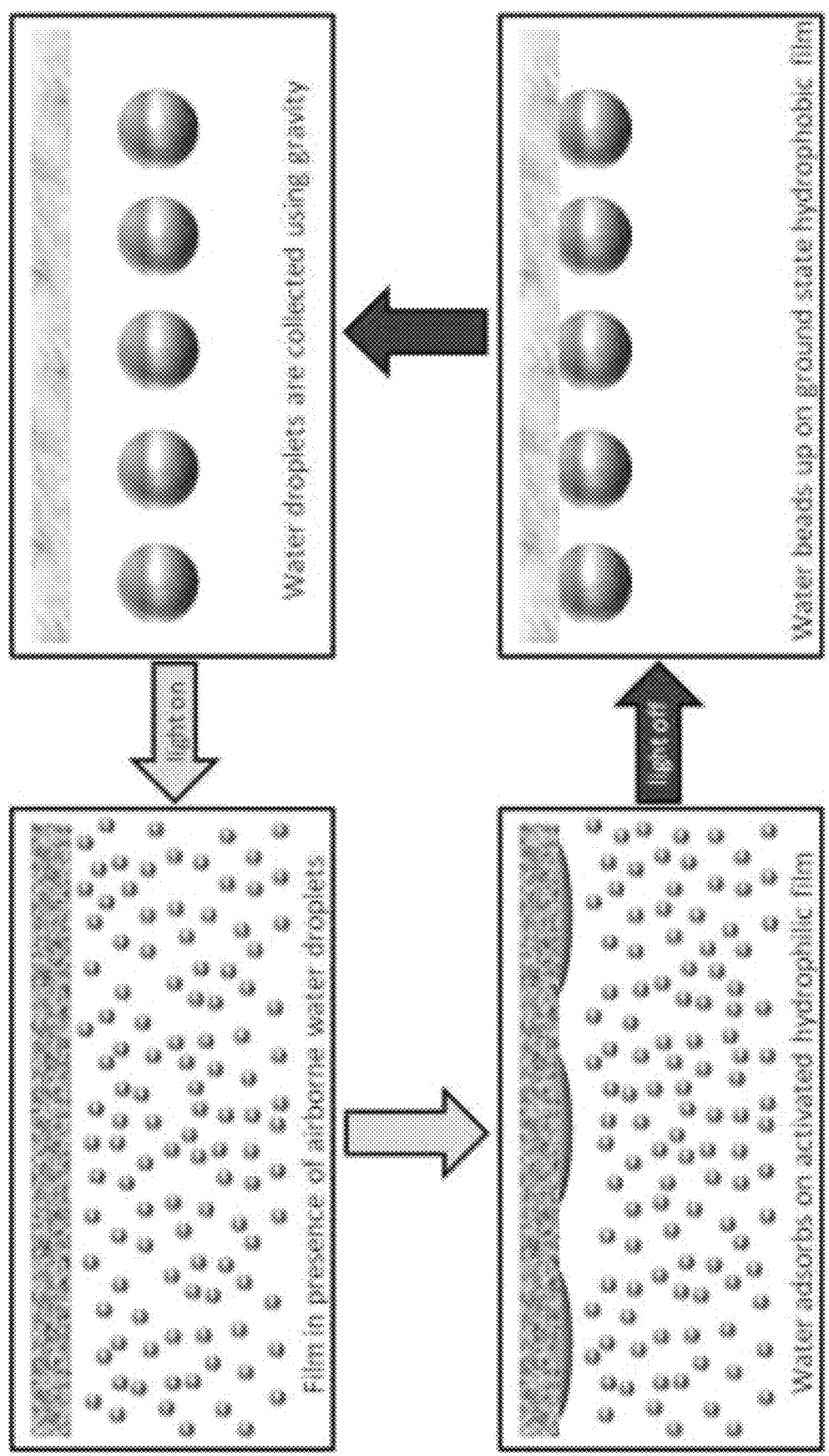
FIG. 2.

Unless specifically noted otherwise herein, the definitions of the terms used are standard definitions used in the art of organic synthesis and chemical sciences. Exemplary embodiments, aspects and variations are illustrative in the figures and drawings, and it is intended that the embodiments, aspects and variations, and the figures and drawings disclosed herein are to be considered illustrative and not limiting.

An "alkyl" group is a straight, branched, saturated or unsaturated, aliphatic group having a chain of carbon atoms, optionally with oxygen, nitrogen or sulfur atoms inserted between the carbon atoms in the chain or as indicated. A $(C_{1-20})$alkyl, for example, includes alkyl groups that have a chain of between 1 and 20 carbon atoms, and include, for example, the groups methyl, ethyl, propyl, isopropyl, vinyl, allyl, 1-propenyl, isopropenyl, ethynyl, 1-propynyl, 2-propynyl, 1,3-butadienyl, penta-1,3-dienyl, penta-1,4-dienyl, hexa-1,3-dienyl, hexa-1,3,5-trienyl, and the like. An alkyl group may also be represented, for example, as a —$(CR^1R^2)$m- group where $R^1$ and $R^2$ are independently hydrogen or are independently absent, and for example, m is 1 to 8, and such representation is also intended to cover both saturated and unsaturated alkyl groups.

An alkyl as noted with another group such as an aryl group, represented as "arylalkyl" for example, is intended to be a straight, branched, saturated or unsaturated aliphatic divalent group with the number of atoms indicated in the alkyl group (as in $(C_{1-20})$alkyl, for example) and/or aryl group (as in $(C_{5-14})$aryl or $(C_{6-14})$aryl, for example) or when no atoms are indicated means a bond between the aryl and the alkyl group. Nonexclusive examples of such group include benzyl, phenethyl and the like.

An "alkylene" group is a straight, branched, saturated or unsaturated aliphatic divalent group with the number of atoms indicated in the alkyl group; for example, a —$(C_{1-3})$alkylene- or —$(C_{1-3})$alkylenyl-.

A "cyclyl" such as a monocyclyl or polycyclyl group includes monocyclic, or linearly fused, angularly fused or bridged polycycloalkyl, or combinations thereof. Such cyclyl groups include the heterocyclyl analogs. A cyclyl group may be saturated, partially saturated or aromatic.

"Halogen" or "halo" means fluorine, chlorine, bromine or iodine.

A "heterocyclyl" or "heterocycle" is a cycloalkyl wherein one or more of the atoms forming the ring is a heteroatom that is a N, O, or S. Non-exclusive examples of heterocyclyl include piperidyl, 4-morpholyl, 4-piperazinyl, pyrrolidinyl, 1,4-diazaperhydroepinyl, 1,3-dioxanyl, and the like.

"Substituted or unsubstituted" or "optionally substituted" means that a group such as, for example, alkyl, aryl, heterocyclyl, $(C_{1-8})$cycloalkyl, heterocyclyl$(C_{1-8})$alkyl, aryl $(C_{1-8})$alkyl, heteroaryl, heteroaryl$(C_{1-8})$alkyl, and the like, unless specifically noted otherwise, may be unsubstituted or, may substituted by 1, 2 or 3 substituents selected from the group such as halo, nitro, trifluoromethyl, trifluoromethoxy, methoxy, carboxy, —$NH_2$, —OH, —SH, —$NHCH_3$, —$N(CH_3)_2$, —SMe, cyano and the like.

The following procedures may be employed for the preparation of the compounds of the present invention. The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In some cases, protective groups may be introduced and finally removed. Suitable protective groups for amino, hydroxy, and carboxy groups are described in Greene et al., *Protective Groups in Organic Synthesis*, Second Edition, John Wiley and Sons, New York, 1991. Standard organic chemical reactions can be achieved by using a number of different reagents, for examples, as described in Larock: *Comprehensive Organic Transformations*, VCH Publishers, New York, 1989.

EXAMPLES

Example 1

Preparation of a Photo-Switchable Surface

A photo-switchable surface was prepared by a 2-step synthesis of the spiropyran 3',3'-dimethyl-6-nitro-1'-octadecylspiro[chromene-2,2'-indoline], III or "C-18-spiropyran," which is then followed by a third step in which the spiropyran III and a polymer were dissolved in solvent, coated onto a substrate, and the resultant polymer film dried. The photo-switchable polymer surface was characterized by drop-shape analysis of water on the surface.

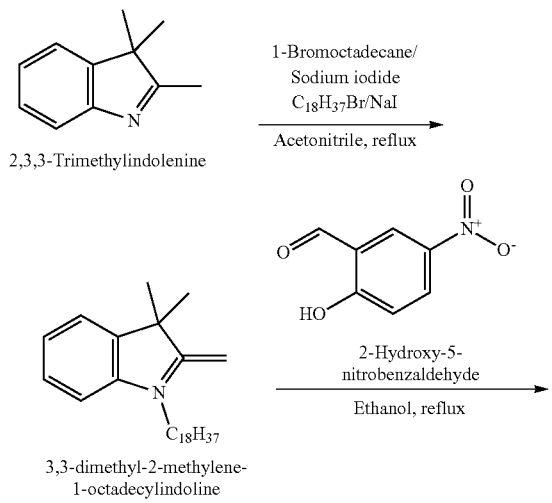

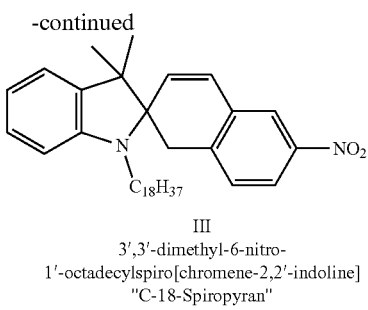

III
3',3'-dimethyl-6-nitro-
1'-octadecylspiro[chromene-2,2'-indoline]
"C-18-Spiropyran"

Compound III is a specific compound of formula I, in which X=4-nitro (4-NO$_2$); m is 1; n=0 (no Y substituents other than H); R=n-octadecyl (n-C$_{18}$H37); and Z=C(CH$_3$)$_2$.

A. Synthesis of intermediate 3-dimethyl-2-methylene-1-octadecylindoline

To a 500-mL, three-necked, round bottom flask was added 10.0 mL 2,3,3-trimethylindolenine (62 mmol, 1.0 equivalent), 9.34 g sodium iodide (62 mmol, 1.0 equivalent) and 200 mL of acetonitrile. The mixture was heated to reflux with stirring. To the refluxing solution, 19.2 mL of bromooctadecane (56 mmol, 0.9 equivalent) was added dropwise. The solution was refluxed for 7 days (158 hours), with occasional additions of acetonitrile to maintain solvent volume.

The solvent was removed by evaporation with heating, and the residue was cooled to room temperature. The residue was extracted into acetonitrile. The filtrate was concentrated under reduced pressure. The residue was dissolved in methylene chloride and transferred to a separatory funnel. The solution was washed with saturated sodium bicarbonate solution two times and water once. The organic phase was dried over sodium sulfate and concentrated under reduced pressure. The crude yield of 3-dimethyl-2-methylene-1-octadecylindoline was 23.43 grams. The material was used in the next step without purification.

B. Synthesis of C-18-Spiropyran, Compound III 6.71 grams of 5-nitrosalicylaldehyde (40 mmol, 1.0 equivalent) was added to 150 mL ethanol in a round bottom flask and brought to reflux. To the refluxing solution was added dropwise 16.54 grams of the crude product from step 1, namely, 3-dimethyl-2-methylene-1-octadecylindoline (40 mmol, 1.0 equivalent). The mixture was refluxed overnight. After refluxing, the solution was cooled to room temperature and filtered. The solid was washed with ice-cold ethanol and dried under vacuum, to yield 12.80 grams of purple crystals of C-18-spiropyran III.

C. Preparation of C-18-Spiropyran Films 0.5 grams of C-18-spiropyran (III) was dissolved in a solution consisting 0.225 grams of poly(methyl methacrylate) (PMMA) (Alfa Aesar Z007-239, average molecular weight 550,000 g/mol) dissolved in 6.5 grams of ethyl acetate. The resulting solution was coated 0.005-inch thick onto Dupont 6638 polyethylene terephthalate substrate using a wire-wound rod (#5 Meyer rod). The resulting wet film was dried at ambient temperature in the dark. The dried film is composed of 68% C-18-spiropyran (III) and 32% PMMA.

A "control" film consisting of 100% poly(methyl methacrylate) was prepared by coating a solution of 0.225 grams PMMA dissolved in 6.5 grams of ethyl acetate. The resulting solution was coated 0.005-inch thick onto Dupont 6638 polyethylene terephthalate substrate using a wire-wound rod (#5 Meyer rod). The resulting wet film was dried at ambient temperature in the dark. The dried film is composed of 100% PMMA.

Determination of hydrophilic/hydrophobic character of films by contact angle measurement: Three 5-microliter aliquots of de-ionized water droplets were deposited on the surface of each of the two resulting dried films. Contact angles were measured for each droplet using a KRÜSS DSA100 Drop Shape Analyzer. Each film was then exposed to 365-nanometer (ultraviolet) light for 5 minutes in a Spectrolinker XL-1500 UV crosslinker (Spectronics Corporation).

The control film remained colorless after exposure to ultraviolet light. The film composed of 68% C-18-spiropyran (III)/32% PMMA was colored purple as a result of the ultraviolet light exposure. Immediately after ultraviolet light exposure, three 5-microliter aliquots of de-ionized water droplets were deposited on the surface of each of the two films, and the contact angles measured. The film composed of 68% C-18-spiropyran (III)/32% PMMA was then stored in the dark at ambient temperature for two days. Contact angles of three 5-microliter water droplets on the now-deactivated film were then determined.

Results of the series of contact angle measurements are given in Table 1.

TABLE 1

Contact angles for 5-microliter deionized water droplets on 100% poly(methyl methacrylate) (PMMA) films and 68% C-18-spiropyran (III)/32% PMMA film pre- and post-ultraviolet light exposure.

|  | 100% PMMA film | 100% PMMA film post-ultraviolet exposure | 68% C-18-spiropyran (III)/32% PMMA film | 68% C-18-spiropyran (III)/32% PMMA film post-ultraviolet exposure | 68% C-18-spiropyran (III)/32% PMMA film post-ultraviolet exposure followed by 2 days in darkness |
| --- | --- | --- | --- | --- | --- |
| Droplet 1 | 77.1° | 75.5° | 102.2° | 79.4° | 89.4° |
| Droplet 2 | 85.4° | 79.4° | 97.9° | 76.2° | 85.1° |
| Droplet 3 | 82.7° | 80.0° | 98.1° | 74.4° | 84.4° |
| Average ± standard deviation | 81.7° ± 4.2° | 78.3° ± 2.4° | 99.4° ± 2.4° | 76.7° ± 2.5° | 86.3° ± 2.7° |

Water droplets on the film composed of 100% PMMA show an average contact angle of 81.7°±4.2°. Following exposure to ultraviolet light, the average contact angle is 78.3°±2.4°, a change which shows little statistical significance (p=0.31). The contact angles are all slightly less than 90°, indicating that the 100% PMMA film is slightly hydrophilic.

Water droplets on the film composed of 68% C-18-spiropyran (III)/32% PMMA show an average contact angle of 99.4°±2.4°. The angle is greater than 90°, indicating the film is hydrophobic. Following exposure to ultraviolet light, the average contact angle is 76.7°±2.5°, a statistically-significant (p=0.0003) decrease of 22.7°. The post-ultraviolet exposure contact angle is less than 90°, indicating the ultraviolet-exposed 68% C-18-spiropyran (III)/32% PMMA film has an increased hydrophilicity.

After two subsequent days in the dark, the previously-exposed 68% C-18-spiropyran (V)/32% PMMA film shows an average contact angle of 86.3°±2.7°. The dark-reversed film shows a recovery of the hydrophobicity, as measured by a significant (p=0.01) increase of the contact angle by 9.6° as compared to the contact angle measured for the film immediately after exposure to ultraviolet light. After two days in the dark, the film does not show complete recovery of the hydrophobicity, as measured by a still significantly (p=0.003) reduced contact angle, 13.1° less than the film pre-exposure.

Example 2

Synthesis of C1-H, C4-H, C4-OMe, C8-H, and C18-OMe Spiropyrans and Solution Preparation A. General Synthetic Route to Spiropyrans

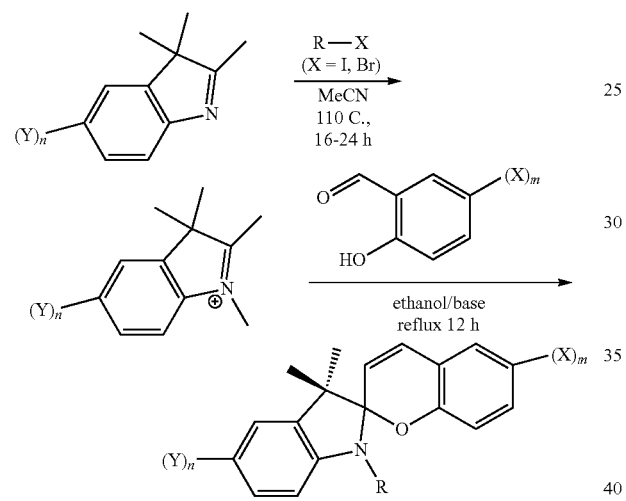

These spiropyrans were prepared using an adapted version of the procedure in Tomasulo, Massimiliano et al., Journal of Organic Chemistry (2007), 72(2):595-605.

B. 5'-methoxy-3',3'-dimethyl-6-nitro-1'-octadecyl-spiro[chromene-2,2'-indoline] (C18-OMe)

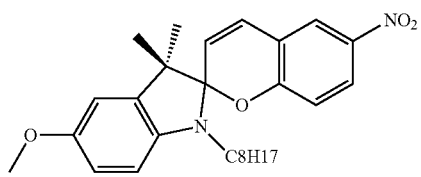

C18-OMe spiropyran is a specific compound of formula I, in which X=4-nitro (4-NO2); m is 1; Y=methoxy (OCH$_3$); n=1; R=n-octadecyl (n-C$_{18}$H$_{37}$); and Z=C(CH$_3$)$_2$, and was prepared as follows.

A solution of the iodide salt of 5-methoxy-3,3-dimethyl-2-methylene-1-octadecyl-indoline (2 g, 3.72 mmol), 2-hydroxy-5-nitro-benzaldehyde (0.65 g, 3.91 mmol, Ark Pharm Inc., Libertyville, Ill.), and triethylamine (0.8 mL, 5.56 mmol, Sigma Aldrich, St. Louis, Mo.) in ethanol (20 mL) was heated for 12 h under reflux and a nitrogen blanket. After cooling down to room temperature, the solvent was removed under reduced pressure. The residue was extracted with dichloromethane (2×20 mL) and washed with distilled water (20 mL). The organic layer was dried over anhydrous Na2SO4 and removed under reduced pressure to get the crude product. The crude was suspended in hexane and the solid was filtered to afford the desired product (1.48 g, 68%). $^1$H NMR (400 MHz, DMSO-d6): δ 10.18 (br s, 1H), 8.60 (s, 1H), 8.29-8.28, m, 2H), 7.80 (d, J=8.28, 1H), 7.53 (d, J=8.28, 1H), 7.09 (d, J=2.44, 1H), 6.90 (d, J=9.8, 1H), 6.25 (d, J=9.8, 1H), 3.11 (m, 2H), 1.78-1.76 (m, 2H), 1.68 (s, 6H), 1.50-1.20 (m, 13H). LCMS (M+1): 442.4.

C. 1',3'-dihydro-3',3'-dimethyl-6-nitro-1'-octyl-spiro[2H-1-benzopyran-2,2'-[2H]indole] (C8-H)

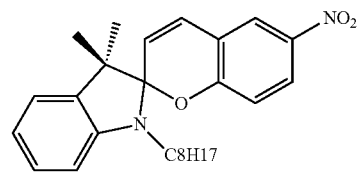

C8-H spiropyran is a specific compound of formula I, in which X=4-nitro (4-NO$_2$); m is 1; n=0 (no Y substituents other than H); R=n-octyl (n-C$_8$H$_{17}$); and Z=C(CH$_3$)$_2$. C8-H was prepared in accordance with the procedure in Wu, Yusong et al., Journal of Physical Chemistry B (2008), 112(25): 7530-7536.

D. 1'-butyl-1',3'-dihydro-3',3'-dimethyl-6-nitro-spiro[2H-1-benzopyran-2,2'-[2H]indole] (C4-H)

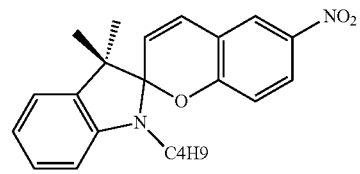

C4-H spiropyran is a specific compound of formula I, in which X=4-nitro (4-NO$_2$); m is 1; n=0 (no Y substituents other than H); R=n-butyl (n-C$_4$H$_9$); and Z=C(CH$_3$)$_2$. C8-H was prepared as in C above.

E. 5'-methoxy-3',3'-dimethyl-6-nitro-1'-octadecyl-spiro[chromene-2,2'-indoline] (C$_4$—OMe)

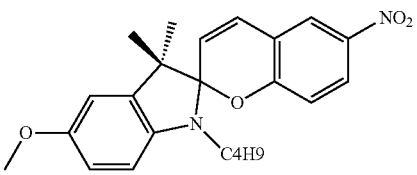

C4-OMe spiropyran is a specific compound of formula I, in which X=4-nitro (4-NO$_2$); m is 1; Y=methoxy (OCH$_3$); n=1; R=n-butyl (n-C$_4$H9); and Z=C(CH$_3$)$_2$. C4-OMe was prepared as in B above.

A solution of the iodide salt of 1'-butyl-5'-methoxy-3',3'-dimethyl-6-nitro-spiro[chromene-2,2'-indoline] (2.21 g, 9.39 mmol), 2-hydroxy-5-nitro-benzaldehyde (1.64 g, 9.86 mmol) and triethylamine (2.62 mL, 18.79 mmol) in ethanol (20 mL) was heated for 12 h under reflux and a nitrogen blanket. After cooling down to room temperature, the solvent was removed under reduced pressure. The residue was extracted with dichloromethane (2×20 mL) and washed with distilled water (20 mL). The organic layer was dried over anhydrous $Na_2SO_4$ and removed under reduced pressure to get the crude product. The crude was suspended in hexane and the solid was filtered to afford the desired product (1.48 g, 48%). $^1H$ NMR (400 MHz, DMSO-d6): δ 10.18 (br s, 1H), 8.60 (s, 1H), 8.29-8.28, m, 2H), 7.80 (d, J=8.28, 1H), 7.53 (d, J=8.28, 1H), 7.09 (d, J=2.44, 1H), 6.90 (d, J=9.8, 1H), 6.25 (d, J=9.8, 1H), 3.11 (m, 2H), 1.78-1.76 (m, 2H), 1.68 (s, 6H), 1.50-1.20 (m, 13H). LCMS (M+1): 395.2

F. 1',3',3'-trimethyl-6-nitro-spiro[chromene-2,2'-indoline] (C1-H)

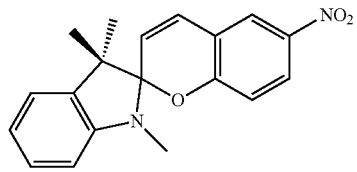

C1-H spiropyran is a specific compound of formula I, in which X=4-nitro (4-$NO_2$); m is 1; n=0 (no Y substituents other than H); R=methyl ($CH_3$); and Z=C($CH_3$)$_2$. C1-H was prepared in accordance with the procedure in Shiraishi, Yasuhiro et al., *Organic Letters* (2009), 11(15): 3482-3485.

G. 3',3'-dimethyl-6-nitro-1'-[(4-vinylphenyl)methyl]spiro[chromene-2,2'-indoline] (Styrene-H)

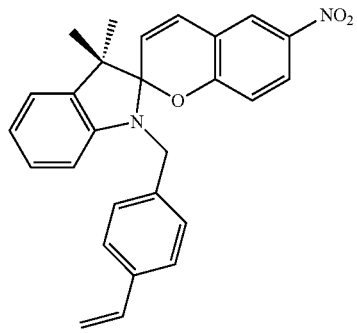

Styrene-H spiropyran is a specific compound of formula I, in which X=4-nitro (4-$NO_2$); m is 1; n=0 (no Y substituents other than H); R=styrene; and Z=C($CH_3$)$_2$. Styrene-H was prepared in accordance with the procedures in Tan, Chunbin et al., *Huaxue Xuebao* (2012), 70(9): 1095-1103 and Tian, Zhiyuan et al., *Journal of the American Chemical Society* (2011), 133(40): 16092-16100.

H. Preparing Small Molecule Solutions

Poly(methyl methacrylate) (450 mg, PMMA, Alfa Aesar, Ward Hill, Mass.) was added to 13 g (14.4 mL) of ethyl acetate. The PMMA was dissolved in ethyl acetate under agitation for 12 h. 250 mg of each SP (including C18-H, as prepared in Example 1) was added to 3.375 g of the PMMA/ethyl acetate solution and agitated until dissolved. The resulting solutions were 10% solids by mass and 69:31 SP/PMMA by mass.

Example 3

Synthesis of P(SP-homo), P(SP-co-MMA) (1:1), P(SP-co-MMA) (1:3), P(SP-co-MMA) (1:5), and P(SP-co-MMA) (1:10) and Solution Preparation

A. P(SP-homo)

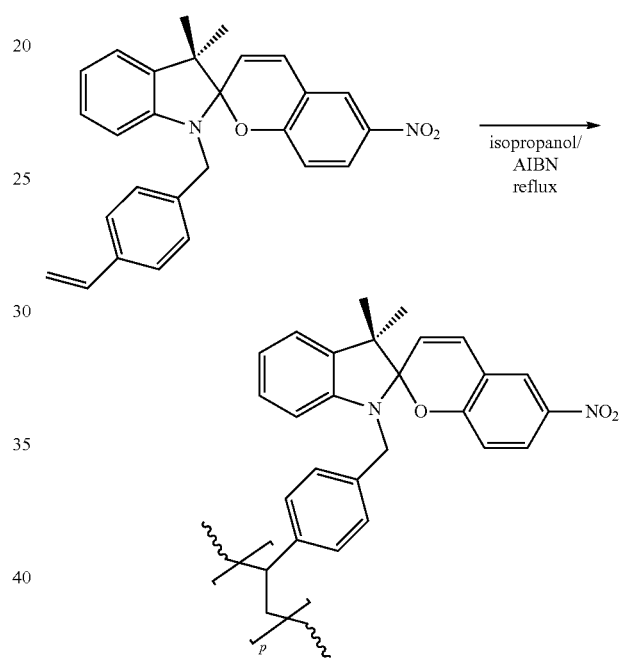

P(SP-homo) is a specific compound of formula II, in which X=4-nitro(4-$NO_2$); m is 1, n=0 (no Y substituents other than H); Z=C($CH_3$)$_2$; and p=unknown. R''' and q are not applicable.

A 50 mL round bottom flask was charged with Styrene-H (1 g, 0.0259 mol), as prepared in Example 2G, and isopropanol (10 mL). The mixture was degassed with nitrogen for 5 minutes, then heated and stirred at 75° C. In a separate vial, 40 mg of 2,2'-Azobis(2-methylpropionitrile) (AIBN, Sigma Aldrich, St. Louis, Mo.) was dissolved in 2 mL of isopropanol and degassed with nitrogen. The AIBN solution was added to the hot Styrene-H and isopropanol reaction mixture and heated and stirred at 75° C. for 15 h. The reaction mixture was cooled to room temperature. The resulting solid was filtered, washed with hexanes, and dried in a vacuum oven at 40° C. for 4 h (0.57 g).

$^1H$ NMR (CDCl$_3$) showed 70% polymer and about 30% unreacted monomer. To remove the unreacted monomer, the solid was washed with 1:1 ether/hexanes and ether. The $^1H$ NMR still showed about 20% monomer. The solid was taken back into ether and stirred at room temperature overnight. The solid was filtered and washed with ether. $^1H$ NMR before drying the sample showed pure homopolymer. The solid was dried in a vacuum oven at 40° C. for 8 h (isolated weight 0.25 g).

B. P(SP-co-MMA) (1:1), P(SP-co-MMA) (1:3), P(SP-co-MMA) (1:5), and P(SP-co-MMA) (1:10)

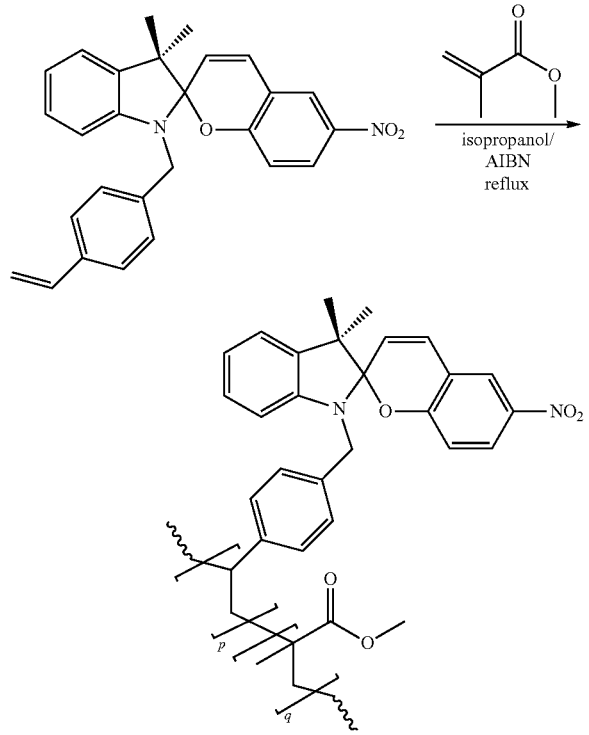

P(SP-co-MMA) (1:1), P(SP-co-MMA) (1:3), P(SP-co-MMA) (1:5), and P(SP-co-MMA) (1:10) are variants of compound II, in which X=4-nitro (4-NO2); m is 1, n=0 (no 7 substituents other than H); Z=C(CH3)2; p=unknown; R'''=methyl methacrylate (MMA); and q=unknown. The (1:1), (1:3), (1:5), and (1:10) note the molar rations of Styrene-H to MMA in the copolymers.

A 50 mL round bottom flask was charged with Styrene-H (1 g, 0.0024 mol), as prepared in Example 2G, and isopropanol (8 mL). The resulting slurry was degassed with nitrogen for 5 minutes. Methyl methacrylate (0.26 mL, 0.0024 mol, 1 eqv., Sigma Aldrich, St. Louis, Mo.) was added to the solution. The resulting mixture was degassed for another 5 minutes, then heated and stirred at 75° C. In a separate vial, 40 mg of AIBN was dissolved in 2 mL of isopropanol and degassed with nitrogen. The AIBN solution was added to the hot reaction mixture and heated and stirred at 75° C. for 15-24 h. The reaction mixture was cooled to room temperature and stirred for another 24 h. Hexanes (20 mL) were added and the solution was stirred for 1 h. The resulting solid was filtered, washed with 25% EtOAc/hexanes (10 mL×3), and dried at 45° C. in a vacuum oven for 20 h. This method was repeated for the P(SP-co-MMA) (1:3), (1:5), and (1:10) equivalents using (0.77 mL, 0.0072 mol, 3 eqv.), (1.26 mL, 0.012 mol, 5 eqv.), and (2.57 mL, 0.024 mol, 10 eqv.) of methyl methacrylate, respectively. $^1$H NMRs of all solids appeared clean and showed broad peaks, revealing polymer formation.

C. Preparing Polymer Solutions

The 10% solids by mass P(SP-co-MMA) solutions were prepared by adding 50 mg of each copolymer to 450 mg (0.34 mL) dichloromethane and stirring until dissolved.

Example 4

C18-H Spiropyran Water Uptake and Release Studies

A. C18-H Spiropyran Film on PET Preparation

The C18-H spiropyran solution, as prepared in Example 1H, was cast into films on PET substrate (500 gauge, Melinex 454, DuPont Teijin Films) using a 5 mil coating bar and allowed to dry in the dark under ambient conditions for 12 h.

B. Water Uptake of C18-H Film on PET

All FTIR spectra for this experiment were taken using a diamond ATR crystal. FTIR spectra of the uncoated PET substrate and the C18-H film were taken as controls. The first C18-H film sample was exposed to water vapor for 10 min and FTIR spectra were taken. The second C18-H film sample was exposed to 365 nm UV irradiation for 5 min in the Spectrolinker XL-1000 (Spectronics Corporation) and FTIR spectra were taken immediately after. After UV irradiation, the film was exposed to water vapor for 10 min and FTIR spectra were taken again.

As determined by Florea, L. et al., *Sensors and Actuators B: Chemical* (2012), 175: 92-99, the formation of an absorption band at 1593 cm$^{-1}$ indicates the presence of C=N$^+$ stretching vibrations in the merocyanine form. In the FTIR spectra, both controls and the first sample showed no absorption in this region. However, the second sample showed absorption at 1593 cm$^{-1}$ both before and after exposure to water, with a stronger absorption before exposure.

C. Water Uptake of C18-H Film with Shorter Evaporation Time and Longer Irradiation Time A 50 μL aliquot of C18-H spiropyran solution was deposited onto the surface of a germanium ATR crystal. The ethyl acetate was allowed to evaporate for 10 min, resulting in a film. The C18-H film was then irradiated for 20 min with a 405 nm violet laser. After 20 min, while irradiation continued, 1 mL water was added on top of the film. FTIR spectra were taken at various intervals from t=0 min, the moment the solution was deposited on the crystal, to t=47 min.

In the FTIR spectra, a broad band begins to appear at 3400 cm$^{-1}$ after the addition of water and gradually grows as time goes on. This band corresponds to the hydroxyl stretching vibrations in the water adsorbed to the film.

In order to quantify the water retention of the films, the instrumental drift in the FTIR spectra was corrected for and the difference in absorbance between 3385 cm$^{-1}$ and 4000 cm$^{-1}$ ($\Delta_{Abs}$) was plotted as a function of time. The $\Delta_{Abs}$ was then fitted to an exponential decay equation where t is time, and A, $t_0$, and τ are the fitting parameters:

$$\Delta_{Abs} = A \times \left(1 - e^{-\frac{t-t_0}{\tau}}\right)$$

The $\Delta_{Abs}$ showed a sharp increase after the addition of water, resulting in a $\Delta_{Abs}$ (1 min) irradiated of $1.88 \times 10^{-3}$.

D. Water Uptake of C18-H Film with Longer Evaporation Time and Shorter Irradiation Time A 50 μL aliquot of C18-H spiropyran solution was deposited onto the surface of a germanium ATR crystal. The ethyl acetate was allowed to evaporate for 45 min, resulting in a film. The film was irradiated for 3 min with a 405 nm violet laser. After 3 min, while irradiation continued, 1 mL water was added on top of the film. FTIR spectra were taken at various intervals from t=0 min, the moment the solution was deposited on the crystal, to t=79 min.

Next, 50 μL of the C18-H solution was deposited onto the surface of another germanium ATR crystal. The ethyl acetate was allowed to evaporate for 47 min, after which 1 mL water was added on top of the film. FTIR spectra were taken at various intervals from t=0 min, the moment the solution was deposited on the crystal, to t=58 min.

The $\Delta_{Abs}$ was plotted as a function of time and fitted to an exponential decay equation. The $\Delta_{Abs}$ (1 min) irradiated for the film irradiated for 3 min, at $0.438 \times 10^{-3}$, was less pronounced than the film irradiated for 20 min. The film that was not irradiated at all had the smallest $\Delta_{Abs}$ (1 min) irradiated at $0.342 \times 10^{-3}$.

E. Water Release in Pre-wetted C18-H Film

To prepare the pre-wetted film, 20 μL of water was added to 180 μL of C18-H solution and mixed until homogeneous. A 50 μL aliquot of the resulting solution was deposited onto the surface of a germanium ATR crystal. The film was allowed to dry under ambient light for 5 min, while FTIR spectra were taken at 1 min intervals. The experiment was repeated using a 405 nm violet laser instead of ambient light.

The FTIR spectra show a steep decrease in absorbance from 0 to 5 min in the sample without irradiation and a steadier decrease in absorbance in the sample with irradiation.

F. Water Contact Angle on C18-H Film

A C18-H film on PET was fabricated as described in part A. A control droplet of water was deposited onto the surface of the film and its contact angle was monitored using a KRÜSS DSA100 Drop Shape Analyzer for 80 s.

Another droplet was deposited onto the surface of the film and left to stabilize for 30 s. After 30 s, the film was irradiated in situ with a 405 nm violet laser for 40 s, then allowed to sit for another 10 s. The contact angle of the droplet was monitored the entire time.

The contact angle data show that the 40 sec irradiation results in a 2-degree decrease compared to the control, from 85.5 degrees to 83.5 degrees. Using the Young-Dupré equation, it was estimated that the adhesion energy of the irradiated droplet increased by about 2.5 mN/m.

Example 5

Spiropyran Small Molecule and Polymer Water Uptake Screening Studies

A 20 μL aliquot of SP solution was added onto the surface of a diamond ATR crystal. The solvent was allowed to evaporate for 10 min under ambient light, after which 1 mL of water was added on top of the film. The water uptake was monitored by FTIR. The experiment was performed using each of the SP solutions prepared in Examples 1H and 2F. The experiment was repeated with the film under continuous irradiation in situ by a 405 nm violet laser from the moment of deposition to water uptake.

The $\Delta_{Abs}$ of each SP small molecule and polymer was plotted as a function of time and fitted to an exponential decay equation. The fitting parameters A and τ were used to calculate $\Delta_{Abs}$ (1 min). Next, the ratio R was calculated, where:

$$R = \frac{\Delta_{Abs}(1 \text{ min}) \text{ irradiated}}{\Delta_{Abs}(1 \text{ min}) \text{ not irradiated}}$$

SP small molecules and polymers with the highest values of R and $\Delta_{Abs}$ (1 min) irradiated were judged as the most promising candidates for a light-powered reversible water harvesting system. Greater $\Delta_{Abs}$ (1 min) irradiated values indicated efficient water uptake and greater R values indicated a larger difference in the water uptake efficiencies of the irradiated and non-irradiated SP forms, suggesting better water retention and release.

For the SP small molecules, the resulting R and $\Delta_{Abs}$ (1 min) irradiated values showed that both irradiated and non-irradiated SPs with shorter alkyl chains held water better than those with longer alkyl chains. However, while the water uptake of non-irradiated SPs decreased rapidly with the size of the alkyl chain, the water uptake of the irradiated SPs decreased more gradually.

The effect of the $(Y)_n$—H and —OMe substituents on the R and $\Delta_{Abs}$ (1 min) irradiated values was also investigated. The electron donating methoxy group in the $(Y)_n$ position was expected to stabilize the zwitterionic, hydrophilic merocyanine form. The C4-OMe and C18-OMe compounds showed increased $\Delta_{Abs}$ (1 min) irradiated compared to C4-H and C18-H, respectively, but lower R values.

Of the SP small molecules, C4-H demonstrated the most promise, followed by C18-OMe, C8-H, and C18-H, respectively. C1-H and Styrene-H showed the least desirable results for this application.

For the SP polymers, the P(SP-co-MMA) (1:3), P(SP-homo), and P(SP-co-MMA) (1:5) copolymers respectively show the most efficient water uptake based on their R and $\Delta_{Abs}$ (1 min) irradiated values. The P(SP-co-MMA) (1:3) exhibited the largest R value, accompanied by the second largest $\Delta_{Abs}$ (1 min) irradiated values. The P(SP-homo) demonstrated the highest $\Delta_{Abs}$ (1 min) irradiated values, but low R value. The P(SP-co-MMA) (1:5) has a relatively large R value, but its $\Delta_{Abs}$ (1 min) irradiated values are not as high as those of P(SP-co-MMA) (1:3) or P(SP-homo).

Of the SP polymers, the P(SP-co-MMA) (1:3) and (1:5) copolymers appear to have the most potential as water harvesting systems. Although the P(SP-homo) showed promising $\Delta_{Abs}$ min) and R values, the quality of the film was not desirable. The (1:3) and (1:5) copolymers showed better coating properties. The P(SP-co-MMA) (1:1) and (1:10) copolymers showed the least desirable results for this application.

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope.

The entire disclosures of all documents cited throughout this application are incorporated herein by reference.

What is claimed is:

1. A method for the condensation of water on a surface of a film deposited on a surface of a device, comprising:

exposing the device comprising photoactive, thermally or electrically-active or a combination of a photoactive, thermally active and/or electrically-active film, wherein the film comprises a compound having a ground state that reversibly converts to its activated state upon exposure to light, heat or an electric field, or a combination of light, heat and/or electric field, wherein the activated state of the compound is more polar than the ground state of the compound;

wherein the device is exposed for a sufficient period of time to condense moisture on or capture and adhere water droplets on the surface of the film; and continuously collecting the water formed or collected on the surface of the device.

2. The method of claim 1, wherein the compound is of the formula I:

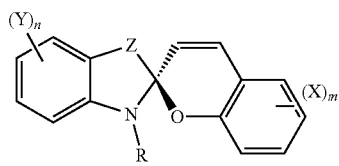

I wherein:

m is 0, 1, 2, 3 or 4;

n is 0, 1, 2, 3 or 4;

R is H or is selected from the group consisting of substituted or unsubstituted $C_{1-22}$ alkyl, substituted or unsubstituted $C_{6-10}$ aryl, substituted or unsubstituted alkyl-$C_{6-10}$ aryl, substituted or unsubstituted $C_{1-22}$ alkylC(O)—, substituted or unsubstituted $C_{1-22}$ alkylS(O)$_{1-2}$—, substituted or unsubstituted $C_{1-22}$ alkylNR'C(O)— and substituted or unsubstituted $C_{1-22}$ alkoxyC(NR'')—, or a polymer;

each X is independently H or is selected from the group consisting of halo, —CN, —NO$_2$, —COOH, —SH, —OH, substituted or unsubstituted $C_{1-6}$ alkyl, substituted or unsubstituted $C_{6-10}$ aryl, substituted or unsubstituted —$C_{1-6}$ alkyl-$C_{6-10}$ aryl, substituted or unsubstituted —$C_{1-6}$alkylC(O)—, substituted or unsubstituted —$C_{1-6}$alkylS(O)$_{1-2}$—, substituted or unsubstituted —$C_{1-6}$ alkylNR'C(O)— and substituted or unsubstituted $C_{1-6}$ alkoxyC(NR'')—;

each Y is independently H or is selected from the group consisting of halo, —CN, —NO$_2$, —COOH, —SH, —OH, substituted or unsubstituted $C_{1-6}$ alkyl, substituted or unsubstituted $C_{6-10}$ aryl, substituted or unsubstituted —$C_{1-6}$ alkyl-$C_{6-10}$ aryl, substituted or unsubstituted $C_{1-6}$ alkylC(O)—, substituted or unsubstituted $C_{1-6}$ alkylS(O)$_{1-2}$—, substituted or unsubstituted $C_{1-6}$ alkylNR'C(O)— and substituted or unsubstituted $C_{1-6}$ alkoxyC(NR'')—;

Z is —O—, —S—, —C(O)—, —C(S)—, —C(NR')—, —S(O)$_{1-2}$—, —NR'— and —CR'R''—; and R' and R'' are each independently selected from the group consisting of H, substituted or unsubstituted $C_{1-6}$ alkyl and substituted and unsubstituted —$C_{1-6}$ alkyl-$C_{6-10}$ aryl.

3. The method of claim 1, wherein R is a polymer deposited on the surface of the device.

4. The method of claim 3, wherein the polymer is selected from the group consisting of polyethylene (LDPE or HDPE), polypropylene, poly(vinyl chloride), poly(vinylidene chloride), polystyrene, polyacrylonitrile, polytetrafluoroethylene (PTFE, Teflon), poly(methyl methacrylate) (PMMA), poly(vinyl acetate) (PVAc), polyisoprene, polychloroprene, poly(oxyethylene) (POE), poly(oxy-1,2-ethanediyloxycarbonyl-1,4-phenylenecarbony (PET), poly[amino(1-oxo-1,6-hexanediyl)], polystyrene, ethyl-vinyl-acetate (EVA), polylactide (PLA), polyhydroxyalkanoates (PHA), polyhydroxybutyrate (PHB), poly-L-lactide (PLLA), PDLA (poly-D-lactide) or mixtures thereof.

5. The method of claim 1, wherein the device is configured for harvesting water from humid air and/or fog.

* * * * *